United States Patent
Höhm et al.

(10) Patent No.: US 10,829,276 B2
(45) Date of Patent: Nov. 10, 2020

(54) DISPENSER FOR A LIQUID

(71) Applicant: Silgan Dispensing Systems Hemer GmbH, Hemer (DE)

(72) Inventors: Sven-Uwe Höhm, Hagen (DE); Heiko Harms, Menden (DE)

(73) Assignee: Silgan Dispensing Systems Hemer GmbH, Hemer (DE)

(*) Notice: Subject to any disclaimer, the term of this patent is extended or adjusted under 35 U.S.C. 154(b) by 0 days.

(21) Appl. No.: 16/481,824

(22) PCT Filed: Oct. 20, 2017

(86) PCT No.: PCT/EP2017/001235
§ 371 (c)(1),
(2) Date: Jul. 29, 2019

(87) PCT Pub. No.: WO2018/141350
PCT Pub. Date: Aug. 9, 2018

(65) Prior Publication Data
US 2020/0055644 A1 Feb. 20, 2020

Related U.S. Application Data

(60) Provisional application No. 62/453,256, filed on Feb. 1, 2017.

(51) Int. Cl.
*B65D 47/18* (2006.01)
*B05B 11/00* (2006.01)
(Continued)

(52) U.S. Cl.
CPC .......... *B65D 47/18* (2013.01); *B05B 11/0067* (2013.01); *B05B 11/04* (2013.01);
(Continued)

(58) Field of Classification Search
CPC ...... B65D 47/18; B65D 47/2056; B65D 1/08; B65D 1/32; B65D 47/2018;
(Continued)

(56) References Cited

U.S. PATENT DOCUMENTS 4,739,906 A * 4/1988 LoTurco ............... A61J 1/1443
222/212
4,938,389 A * 7/1990 Rossi .................... A61F 9/0008
210/321.64
(Continued)

FOREIGN PATENT DOCUMENTS

DE 102010063592 A1 6/2012
WO 2014-048668 A1 4/2014

OTHER PUBLICATIONS

International Search Report and Written Opinion dated Jul. 2, 2018 in International Patent Application No. PCT/EP2017/001235, filed Oct. 20, 2017, English translation attached, all pages.

*Primary Examiner* — Patrick M. Buechner
*Assistant Examiner* — Michael J. Melaragno
(74) *Attorney, Agent, or Firm* — Kilpatrick Townsend & Stockton LLP

(57) ABSTRACT

A discharge device for a liquid medium includes a storage container for receiving a medium, a discharge head which can be secured on the storage container and comprises a discharge opening for discharging the medium out of the storage container, an outlet valve which is paired with the discharge opening and comprises a pretensioned valve element that delimits a valve pre-chamber by means of a pressure application surface formed on a membrane. The pressure application surface has a stationary clamping region on the outside, and a pressure equalization channel which opens into the storage container and comprises a filter assembly that operates microbiologically and is inserted into the pressure equalization channel. The pressure equalization (Continued)

Figure 1:
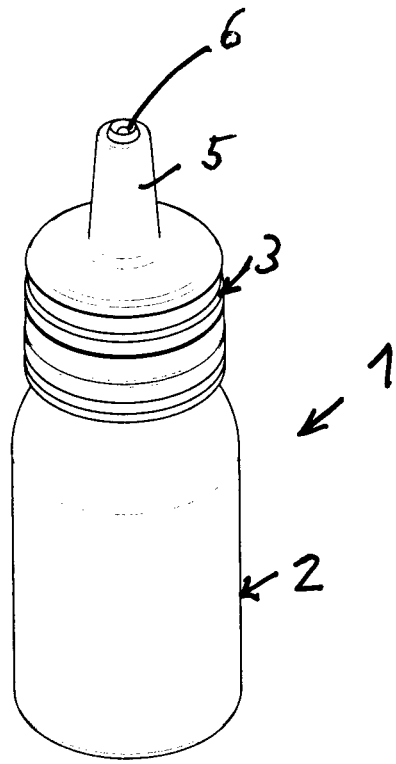

channel is separated from a medium path from the storage container to the discharge opening via the valve pre-chamber, and the pressure application surface has a cap-like edge protrusion as a clamping region which can be placed on a plate edge of the inner component of the discharge head on the inside. The plate edge has a stop that extends outward radially and forms a support surface for the edge protrusion while being spaced from the pressure application surface by a head surface of the plate edge.

17 Claims, 7 Drawing Sheets

(51) Int. Cl.
  *B05B 11/04* (2006.01)
  *B65D 47/20* (2006.01)
  *B65D 1/32* (2006.01)
  *A61F 9/00* (2006.01)
(52) U.S. Cl.
  CPC ............ *B65D 1/32* (2013.01); *B65D 47/2056* (2013.01); *A61F 9/0008* (2013.01)
(58) Field of Classification Search
  CPC ... B05B 11/0067; B05B 11/04; A01G 25/023; A61F 9/0008; A61F 9/0026; B01L 3/0272; B05C 11/1034
  USPC .................. 222/335, 420, 422, 206–215
  See application file for complete search history.

(56) References Cited

U.S. PATENT DOCUMENTS

| | | | | |
|---|---|---|---|---|
| 5,056,689 A * | 10/1991 | Heyl | ............... | A61F 9/0008 222/189.06 |
| 5,105,993 A * | 4/1992 | La Haye | ............... | A61F 9/0008 210/321.89 |
| 5,226,568 A * | 7/1993 | Newton | ............... | B65D 47/2081 222/212 |
| 5,255,826 A * | 10/1993 | Ranalletta | ............ | B05B 11/007 222/209 |
| 5,496,471 A * | 3/1996 | Heyl | ............ | A61F 9/0008 210/266 |
| 5,611,464 A * | 3/1997 | Tsao | ............ | A61K 9/0048 222/189.06 |
| 6,938,800 B1 * | 9/2005 | Lehmkuhl | ............ | B05B 11/047 222/153.14 |
| 7,828,231 B2 * | 11/2010 | Harms | ............ | A61M 15/08 222/321.6 |
| 8,454,828 B2 * | 6/2013 | Wochele | ............ | B05B 11/00444 210/245 |
| 8,616,418 B2 * | 12/2013 | Painchaud | ............ | B65D 47/18 222/422 |
| 8,678,243 B2 * | 3/2014 | Collins | ............ | B05B 11/3056 222/321.6 |
| 8,863,998 B2 * | 10/2014 | Painchaud | ............ | B65D 47/2031 222/494 |
| 9,266,135 B2 * | 2/2016 | Harms | ............ | B05B 11/0059 |
| 9,821,333 B2 * | 11/2017 | Collins | ............ | B05B 11/3011 |
| 10,538,369 B2 * | 1/2020 | Ritsche | ............ | B65D 47/283 |
| 2007/0210115 A1 * | 9/2007 | Stadelhofer | ............ | B05B 1/3447 222/335 |
| 2008/0230633 A1 * | 9/2008 | Harms | ............ | A61M 15/08 239/463 |
| 2011/0068133 A1 * | 3/2011 | Painchaud | ............ | B65D 47/18 222/494 |
| 2011/0155770 A1 * | 6/2011 | Painchaud | ............ | B65D 47/18 222/422 |
| 2014/0069961 A1 * | 3/2014 | Harms | ............ | B05B 11/0059 222/321.6 |
| 2014/0070030 A1 * | 3/2014 | Harms | ............ | B05B 11/0067 239/583 |
| 2014/0203049 A1 * | 7/2014 | Collins | ............ | B05B 11/3004 222/321.6 |
| 2015/0274386 A1 * | 10/2015 | Ritsche | ............ | B05B 11/047 222/335 |
| 2016/0137390 A1 * | 5/2016 | Wochele | ............ | B65D 83/0055 222/206 |
| 2016/0311588 A1 * | 10/2016 | Wochele | ............ | A61J 1/067 |

* cited by examiner

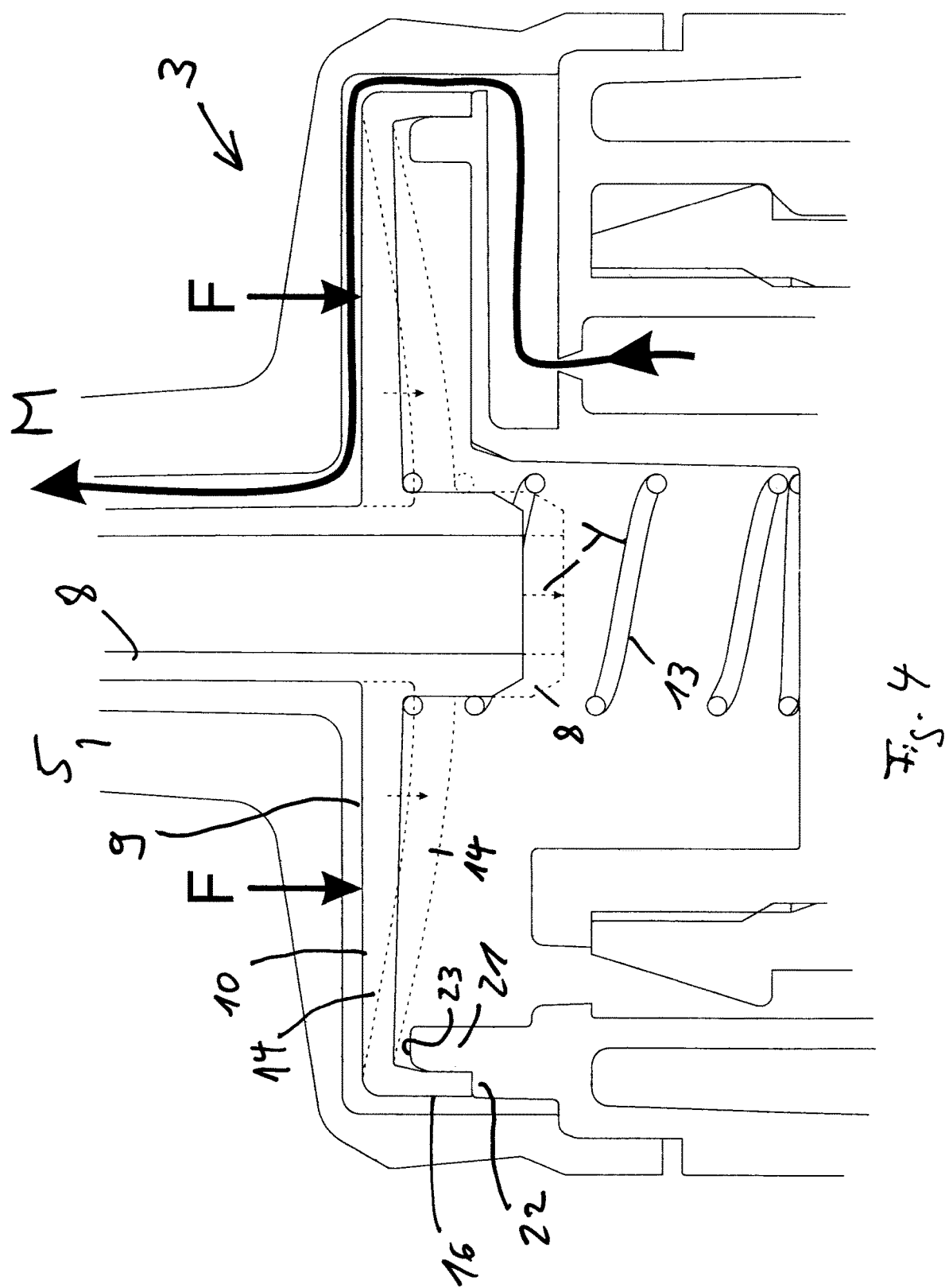

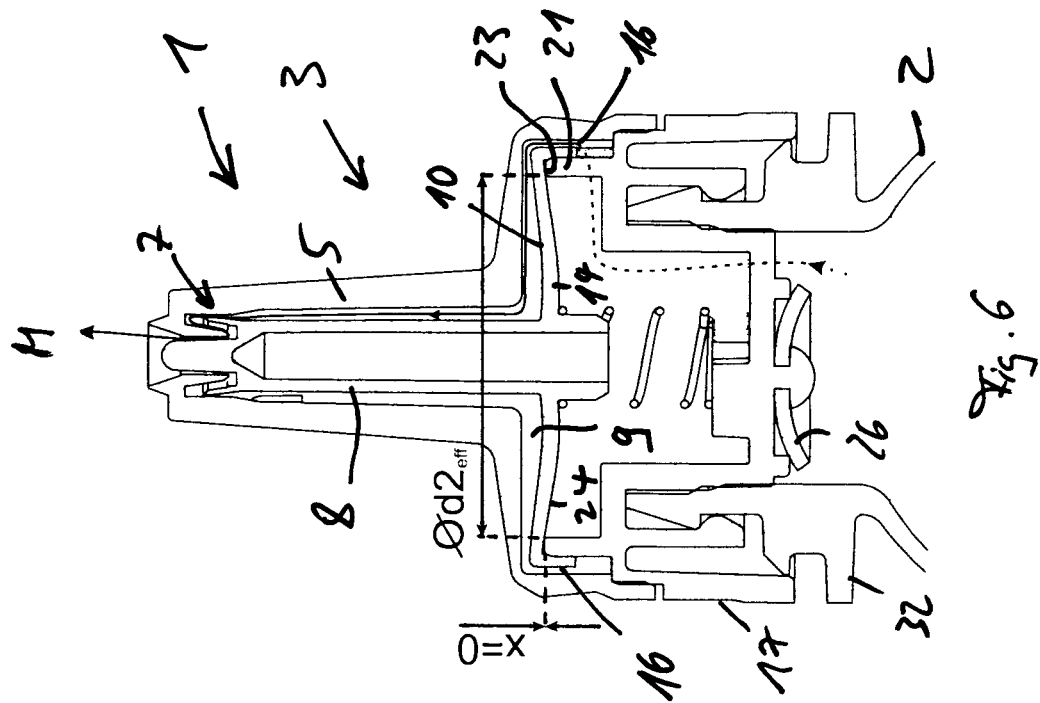
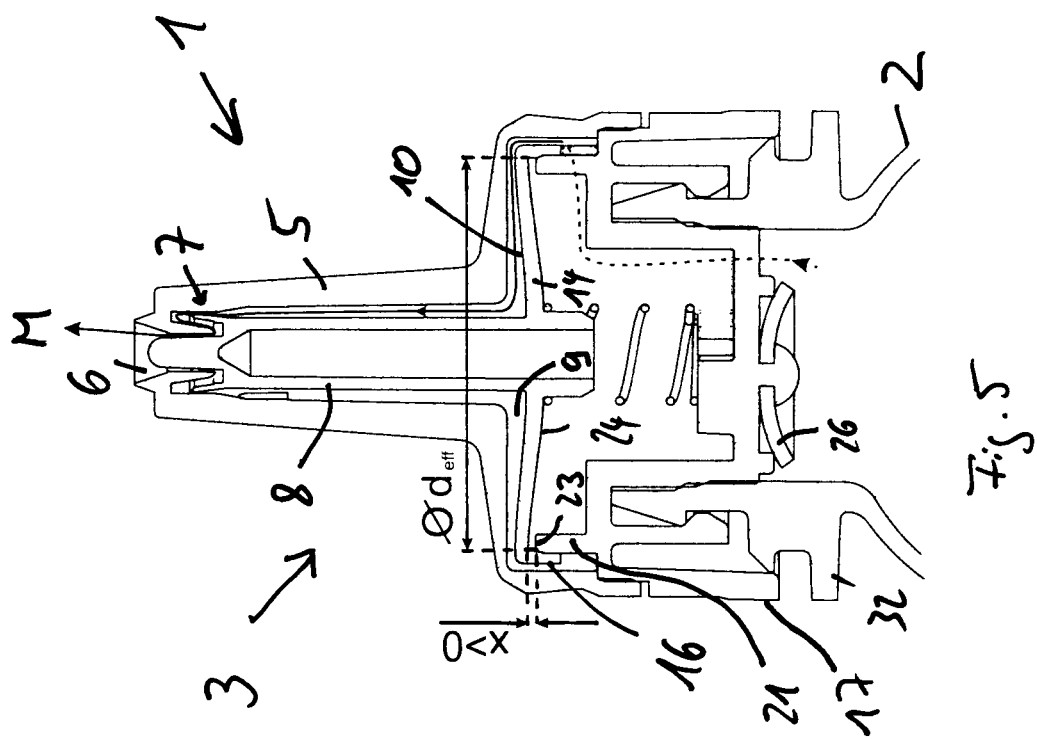

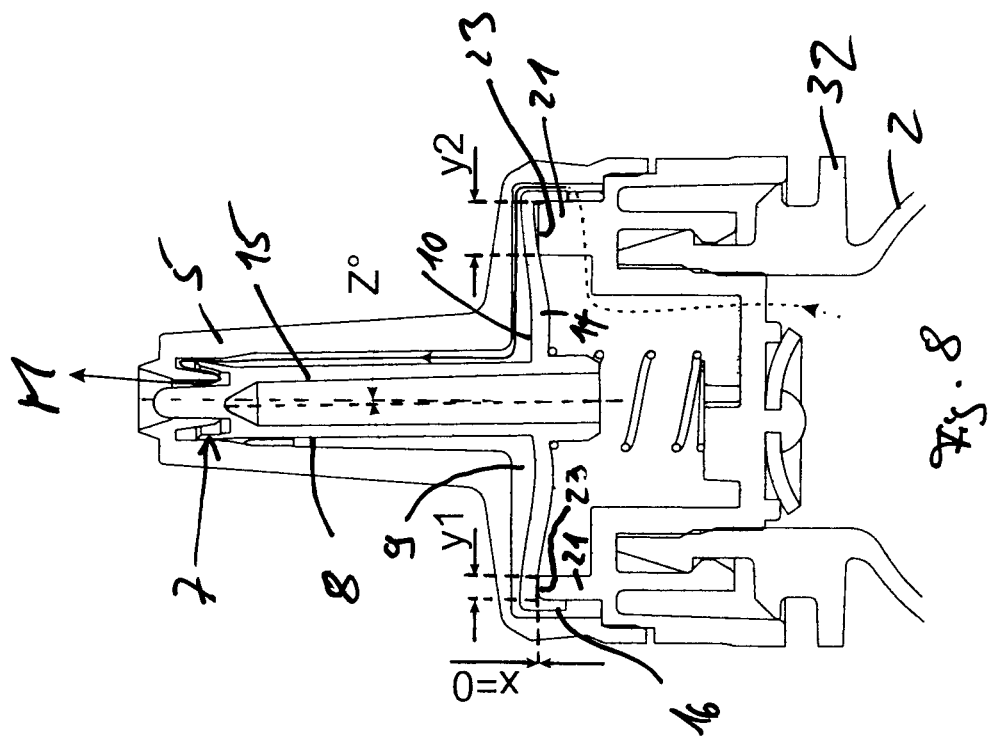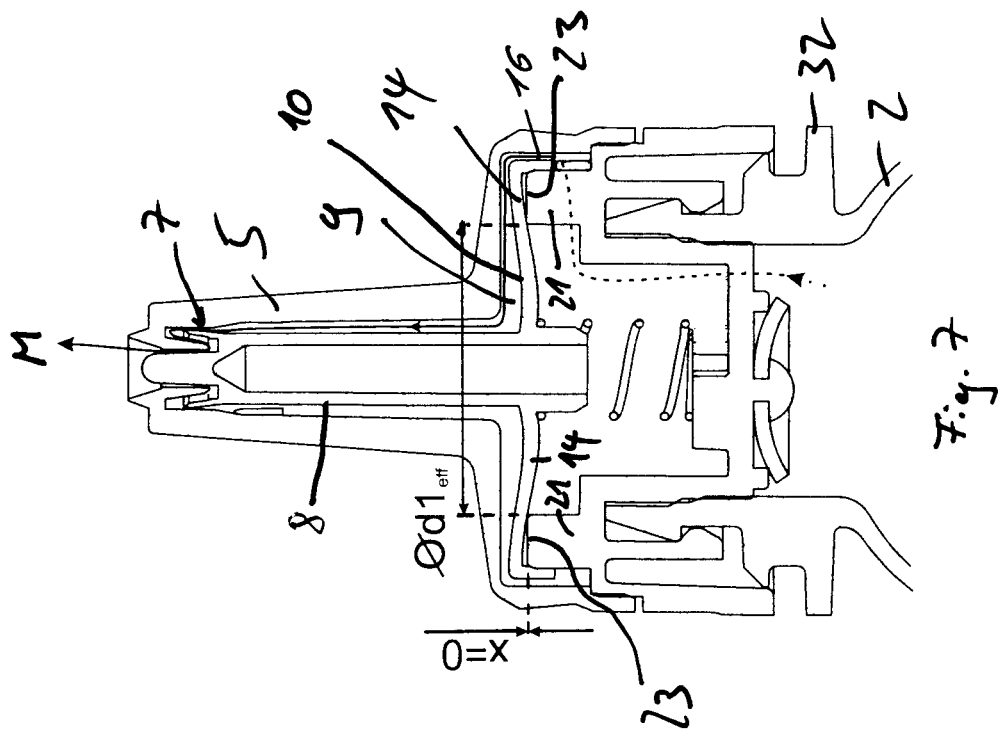

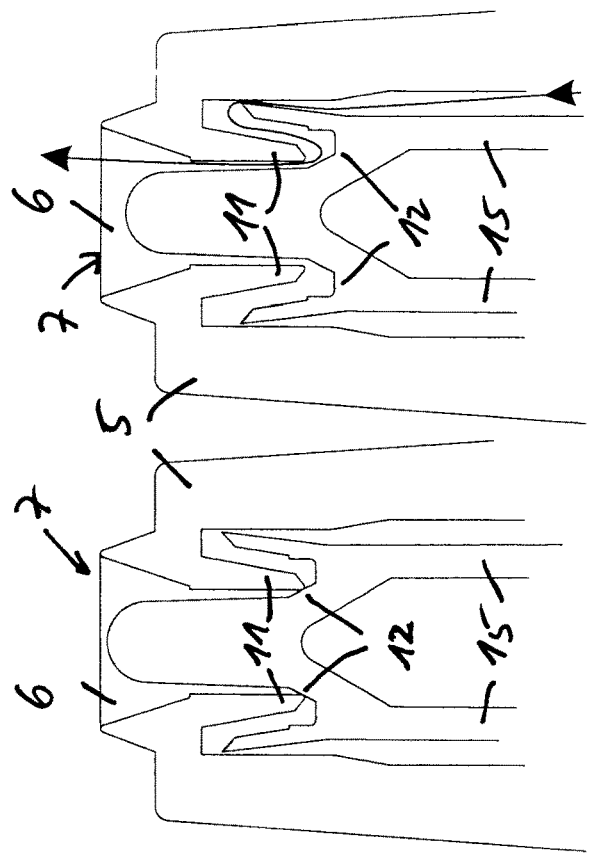
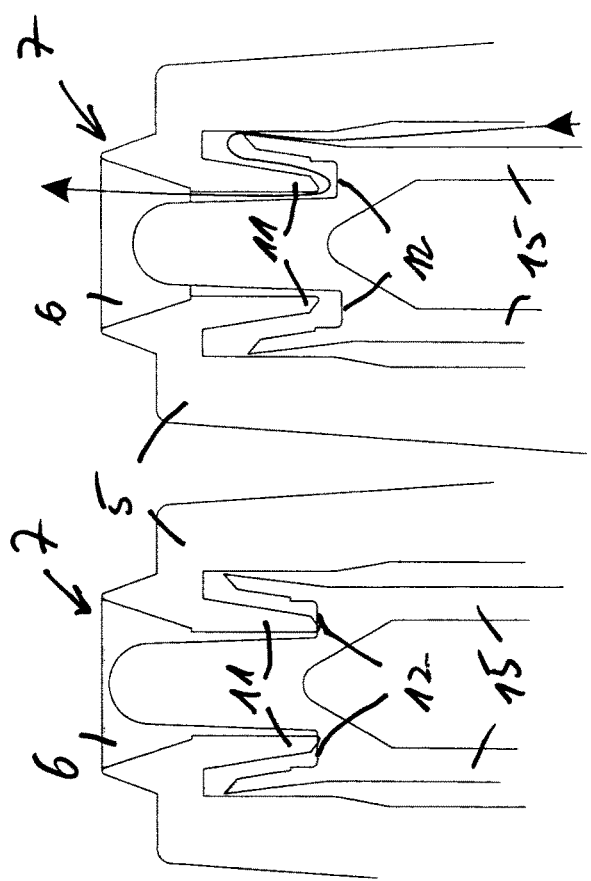

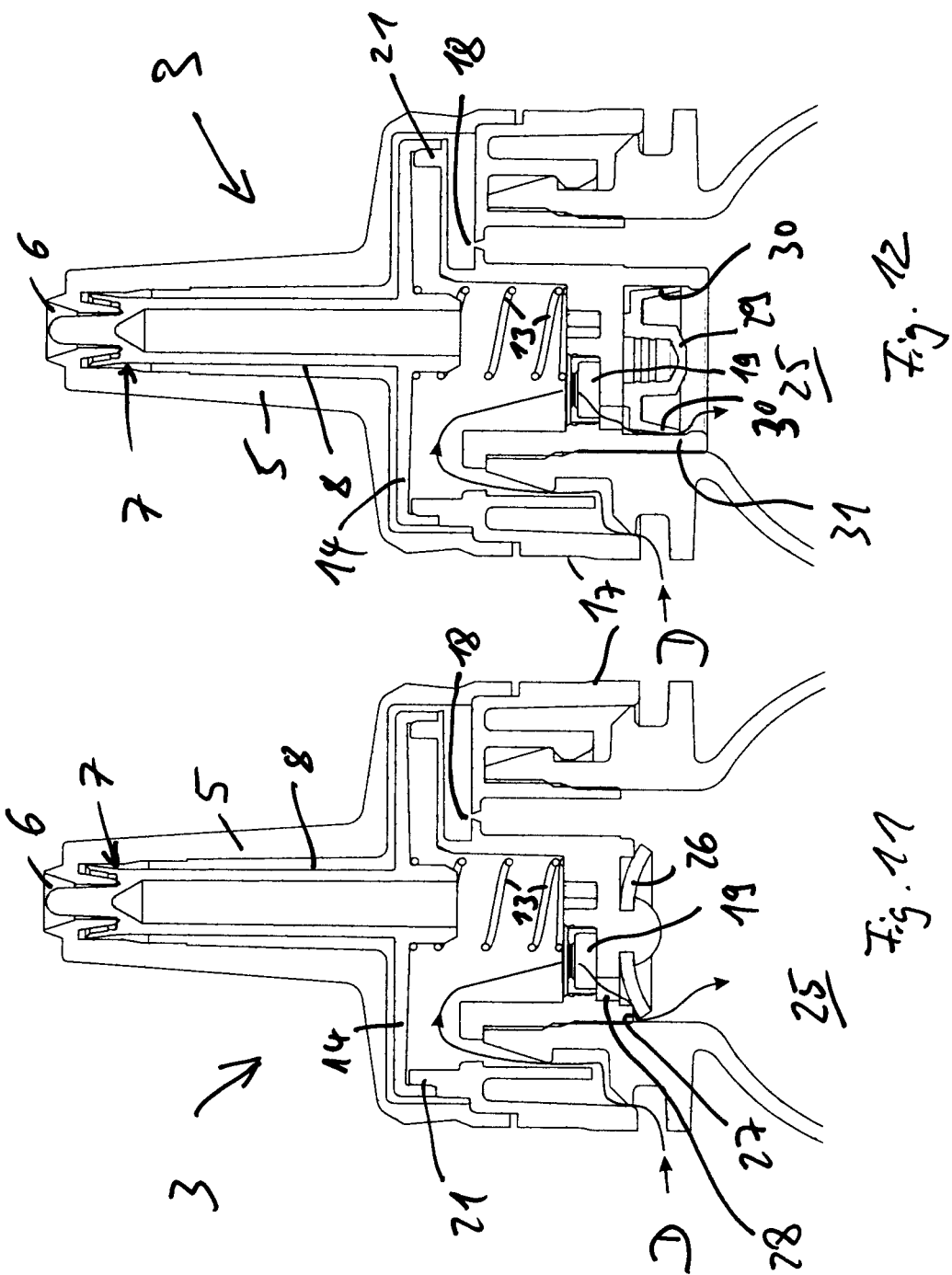

DISPENSER FOR A LIQUID

The invention relates to a dispenser for a liquid according to the preamble of claim 1.

Such a dispenser for a liquid is known from DE 10 2010 063 592 A1. The dispenser in particular is for pharmaceutical purposes and is used for discharging such liquids, specifically for an application of said liquids into the mouth, the nose, the eyes or the ears of a patient. The dispenser has a bottle-like liquid reservoir and a dispensing assembly. The dispensing assembly terminates, at its end which faces away from the liquid reservoir, in a discharge opening which, in a closed state of the dispenser, is closed off by a valve. For this purpose, the valve has a valve seat on the inside of the discharge opening, and a valve body which can be moved relative to the valve seat. Springforce is applied to the valve body such that, in a resting state, said valve body abuts against the valve seat such that the discharge opening is separated from a valve ante chamber. The valve antechamber is delimited at the outside by an outer component of the dispensing assembly. The valve ante chamber is delimited at the inside by a pressure application surface of the valve body. As soon as the liquid pressure in the valve ante chamber rises above a limit pressure determined by the size of the pressure application surface and the configuration of the spring, said pressure brings about a partial displacement of the valve body and lifting-off of the valve body from the valve seat. Here, merely an outside clamping region is positionally invariant. The displacement in particular of a closing pin of the valve body in relation to the valve seat makes it possible for liquid to flow out through the discharge opening.

In the case of the dispenser already known, the valve spring is of relatively weak form. It pushes the valve body against the valve seat with a force of preferably between 2 N and 3 N. Combined with a relatively large pressure application surface, the result is that the discharge opening already opened at a relatively low positive pressure in the valve ante chamber, in the present case at 0.3 bar. The liquid from the valve ante chamber therefore flows through the discharge opening in a state of only low pressure application, which is for the intended making of a drop at the outlet side of the discharge opening. In the case of the known dispenser, it is provided that the generation of pressure in the valve ante chamber is realized by the liquid reservoir, in the form of a bottle, being manually compressed. The consequently increasing pressure in the liquid reservoir is carried forward to the valve chamber via a liquid path.

However, among those dispensers, there is the problem of microbiological contamination in the area of the valve surfaces at the discharge opening. The low opening pressure, which is for generating drops and is intended to prevent the occurrence of unwanted discharge of a spray jet, has the result that, in the closed state, the valve surface pressure close to the discharge opening of the dispenser is not sufficiently high for reliably preventing impurities from entering the inner region of the dispenser following a discharge process. However, since the intended purpose of said dispenser is normally for the liquid to be discharged to be brought up to the human body or introduced into the human body so as to be received by the body as quickly as possible, there is a great risk of impurities passing into the liquid and, there, bacteria loads are caused which can result in patients becoming ill. Therefore, it is known that at least one valve surface of the dispensing valve is formed such that it is liquid repellent, germicidal and/or against germ growth. The intention is to prevent in this way the progression of the contamination into the dispenser. However, the need to use bacteria-killing or bacteria-growth-preventing designs of valve surfaces of the dispensing valve might be disadvantageous.

It is therefore an object of the invention to provide a dispenser according to the preamble of claim 1, which is designed for the dispensing of drops and at the same time reliably prevents contamination of liquid from the outside. Said object is achieved by the features of claim 1.

Consequently, a dispenser is provided which immediately closes as soon as the liquid pressure in the valve ante chamber is no longer sufficient to bring about an open state and an outflow of liquid, wherein the opening pressure is sensitively settable through the type of outer clamping of the pressure applying surface of the valve body. An entire diaphragm diameter of the pressure applying surface can in this way be made available for the valve opening.

Furthermore, at the inside adjacent to the clamping area according to the invention of the pressure applying surface, it is possible to have at the dispensing head a flat support as a partially supporting ring for a diaphragm, on which diaphragm the pressure applying surface can be formed. If the diaphragm is deformed for a media lift, then, after an initial deformation path of the diaphragm, the latter can come down onto the support at its rim. The effective diameter of the pressure applying surface is reduced according to the radial width of the support, and the active force for diaphragm deformation is reduced because a part of the active force is introduced into the supporting ring of the support. Consequently, an increase in movement resistance occurs while the valve ante chamber is filled for a media lift. The positioning of the diaphragm at the support may be defined as a changing point of forces, which is detectable in a tactile manner, along a deformation path of the diaphragm for, for example, drop dispensing. This improves the controllability of the drop dispensing and can thereby reduce overflowing (jet formation). The haptic event of an stop-type pressure-displacement resistance can provide the user with additional perceptible feedback as to when drop dispensing will be realized. A gradual increase in the force of resistance can be detected.

The force/displacement behavior (tactile feedback) of the diaphragm deformation can be used for different application functions by varying the actuation forces. In this regard, the radial width and height of the support may be chosen individually so as to be able to set the amount of the reduction in the effective diaphragm diameter. It is also possible for the support to be of circumferentially asymmetrical form, which can give rise to tilting of the valve plunger with respect to the dispensing opening. The medium to be discharged at the dispensing opening, in particular drops, can almost be sheared off since a passage for the medium is opened up only partially. Possible cohesive forces, which bring about a kind of adhesion of the drop during the drop dispensing, can be counteracted. It is particularly advantageous that, in this case, the dispenser for a fluid remains easily and reliably actuable, and simple to handle.

If, in particular, the dispenser is intended to be operated upside down, it may furthermore be provided that an aeration path outlet of a pressure equalization channel into the reservoir is able to be closed off via a sealing device, provided at the discharge head, in the manner of a check valve. The sealing device may for example be a sealing disc which is curved in a concave manner with respect to the interior of the reservoir and whose disc boundary is in a state of sealing abutment. The disc boundary may also be provided with sealing lips, which provide the sealing disc with a cork-type abutment behavior at a wall of an aeration path outlet such that a sealing plug is formed.

Further details and advantages of the invention can be learnt from the following description and the dependent claims.

The invention will be discussed in more detail below on the basis of the exemplary embodiments illustrated in the appended figures.

Figure 2:
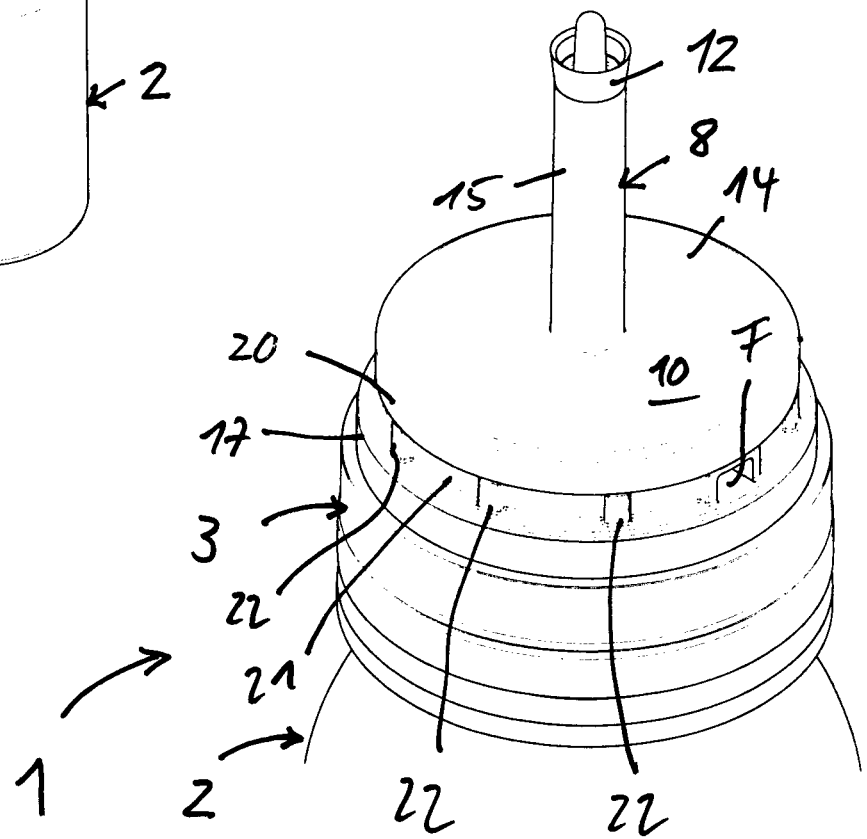
Figure 3:
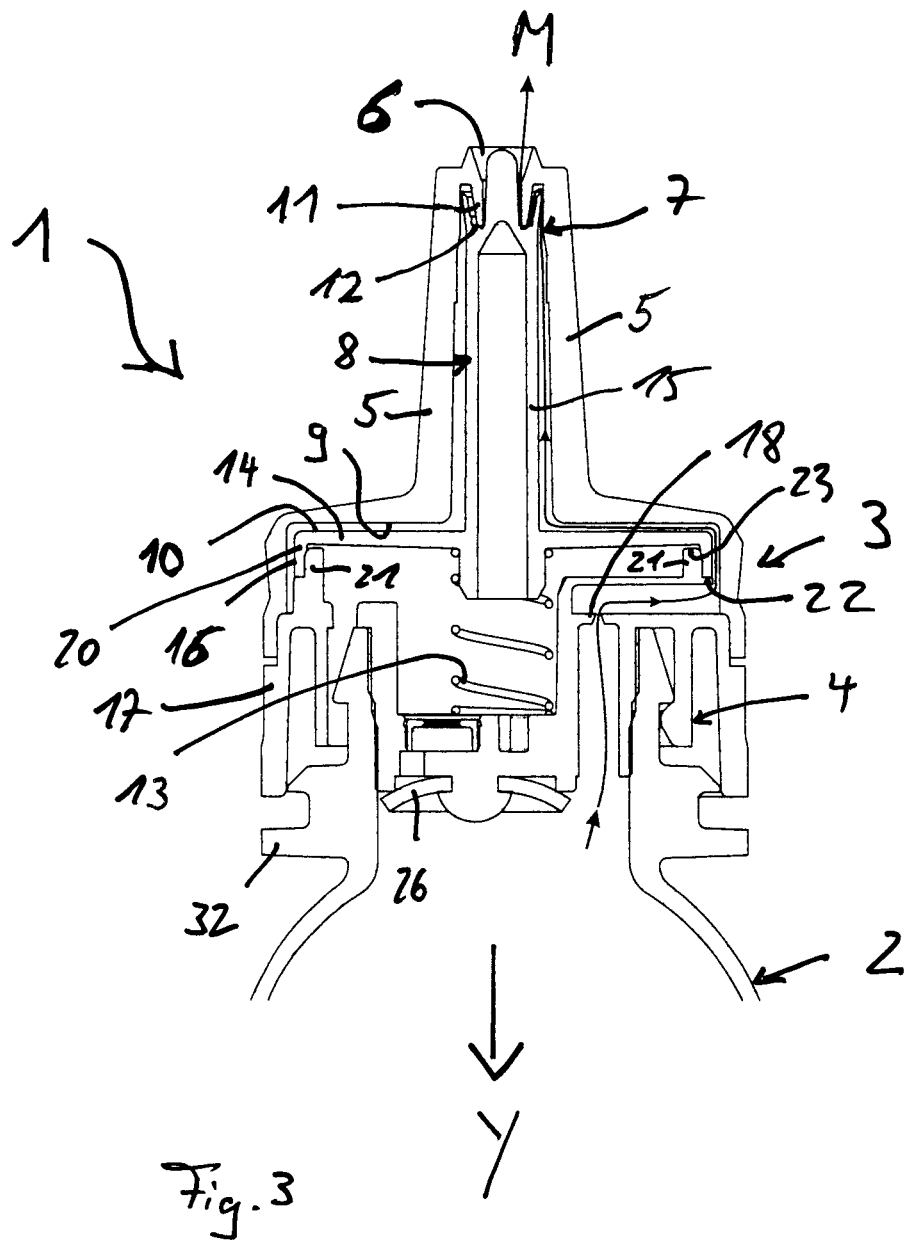

FIG. 1 schematically shows a perspective view of a dispenser with a reservoir container and with a discharge head which has a drop adapter, FIG. 2 schematically shows a perspective view of the discharge head shown in FIG. 1 in an enlarged illustration, leaving out the drop adapter, FIG. 3 schematically shows a longitudinal section of the discharge head according to a first exemplary embodiment, with an illustration of a liquid path, wherein the discharge head is fastened to a neck of a reservoir container, FIG. 4 schematically shows a part of the discharge head according to FIG. 3, with an illustration of diaphragm deformation under media pressure upon actuation, FIG. 5 schematically shows a further longitudinal section of the discharge head according to the first exemplary embodiment, with an illustration of the liquid path and of diaphragm deformation without contact with a disc rim, FIG. 6 schematically shows a longitudinal section of the discharge head according to a second exemplary embodiment, with an illustration of the liquid path and of a diaphragm deformation having a reduced size of a pressure applying surface when the diaphragm touches the disc rim due to a disc rim elevation, FIG. 7 schematically shows a longitudinal section of the discharge head according to a third exemplary embodiment, with an illustration of the liquid path and of a diaphragm deformation having a reduced size of a pressure applying surface when the diaphragm touches the disc rim due to a disc rim elevation and disc rim broadening, FIG. 8 schematically shows a longitudinal section of the discharge head according to a fourth exemplary embodiment, with an illustration of the liquid path and of diaphragm deformation having a reduced size of a pressure applying surface when the diaphragm touches the disc rim due to a disc rim elevation and asymmetrical, circumferential disc rim broadening, FIG. 9a schematically shows in section a design of a valve seat in the discharge opening with flat sealing in a closed state, FIG. 9b schematically shows in section a design of the valve seat in the discharge opening with flat sealing in an open state, FIG. 10a schematically shows in section a design of a valve seat in the discharge opening with conical sealing in a closed state, FIG. 10b schematically shows in section a design of the valve seat in the discharge opening with conical sealing in an open state, FIG. 11 schematically shows a longitudinal section of the discharge head according to the first exemplary embodiment according to FIG. 3, with an illustration of a ventilation path, wherein a sealing disc is provided as a sealing device at a ventilation path outlet into the reservoir, FIG. 12 schematically shows a longitudinal section of the discharge head according to the first exemplary embodiment according to FIG. 3, with an illustration of a ventilation path, wherein a sealing plug is provided as a sealing device at an ventilation path outlet into the reservoir.

FIG. 1 shows a dispenser 1 for a liquid. Said dispenser 1 has a reservoir container 2 to store medium and has a discharge head 3 which is able to be fixed to the reservoir container 2. The reservoir container 2 is preferably of bottle-like form and able to be manually squeezed such that the consequently increasing pressure in the reservoir container 2 causes a medium lift. The discharge head 3 is preferably mounted via a lock 4 (cf. FIG. 4), for example a snap-on lock, to a neck of the reservoir container 2. As per the illustrated exemplary embodiment, the dispenser 1 is designed as a dropper, for example for discharging eye drops.

For this purpose, the discharge head 3 comprises as an exterior component a dispensing adapter, which is a drop per-type adapter 5 in this case. The discharge head 3 has a discharge opening 6 which serves for the discharge of medium from the reservoir container 2 and in which the preferably provided drop per-type adapter 5 terminates at its end which faces away from the reservoir container 2. In a closed state, the discharge opening 6 is able to be closed by a discharge valve 7. The dispensing adapter, provided here as a drop per-type adapter 5, is designed having a tubular extension (FIG. 1).

As FIG. 2 and FIG. 3 show, the discharge valve 7 associated with the discharge opening 6 has a preloaded, in particular spring-preloaded, valve body 8, which delimits a valve ante chamber 9 by way of a pressure applying surface 10. At the area of the discharge opening 6, the discharge valve 7 has an internally valve seat 11 (cf. FIGS. 9a, 9b, 10a, 10b) and in relation to which the valve body 8 is axially movable. By means of a valve spring 13, in particular a pressure spring, force can be applied to the valve body 8 in the direction of the discharge opening 6 such that, in a closed state, said valve body abuts with a sealing edge 12 against the valve seat 11 such that the discharge opening 6 is separated from the valve ante chamber 9. The valve ante chamber 9 is limited on the outside by the drop per-type adapter 5. The valve ante chamber 9 is limited on the inside by the pressure applying surface 10 of the valve body 8. The valve body 8 is designed as pressure applying surface 10 at a diaphragm 14, from which a valve plunger 15, bearing at the head side the sealing edge 12 or some other sealing element 12, rises. The diaphragm 14 and valve plunger 15 are preferably formed in one piece.

The pressure applying surface 10 has on the outside a clamping region 16 that is hold in position. For this purpose, the diaphragm 14 is fastened in a fluid-tight manner, preferably laser-welded, at the boundary side to an inner component 17 of the discharge head 3. The inner component 17 also carries the lock 4 for the fastening to the reservoir container 2.

As soon as the liquid pressure in the valve ante chamber 9 rises above a limit pressure determined by the size of the pressure applying surface 10 and the configuration of the valve spring 13, said pressure brings about a partial shift of the valve body 8 in the direction Y, i.e. the sealing edge 12 lifts away from the valve seat 11 moving of the valve body 8 away from the discharge opening 6. This shift of the valve body 8 allows the liquid to flow through the discharge opening 6. A corresponding liquid path or media path M from the reservoir container 2 via the discharge head 3 and, there, via the valve ante chamber 9 and the discharge valve 7 is indicated in FIG. 3. A flow reducer 18 is preferably provided at the exit from the reservoir container 2. This is a narrow bottleneck through which the medium has to flow to the discharge opening 6 and by which a throttling effect is achieved. The flow resistance of the flow reducer 18 prevents overflowing of the media path F and brings about a pressure drop, being advantageous to allow drops to be dispensed, when the reservoir container 2 is manually squeezed transversely with respect to the axial direction and medium is pressed into the valve ante chamber 9 along the media path M.

According to the dispenser 1 shown in FIG. 1 to FIG. 3, the valve spring 13 is in fact of relatively weak designed. Connected with a relatively large flat pressure applying surface 10, this results in an opening of the discharge opening 6 at a relatively low positive pressure of for example 0.2 to 0.5 bar in the valve ante chamber 9. The medium then flows through the discharge opening 6 applying only low pressure, which serves for the intended drop formation at the discharge opening 6.

The dispenser 1 further has a pressure compensation channel D, which opens into the storage container 2 and has a microbiologically active filter arrangement 19 inserted in said channel, as will be described below in conjunction with FIG. 11 and FIG. 12. The pressure compensation channel D is separated from the media path M.

FIG. 2 to FIG. 4 furthermore show that the pressure applying surface 10 has a clamping area 16 being designed as a cap-like rim projection 20 which can be placed internally on an outer rim of a disc 21 of the inner component 17 of the discharge head 3. For this purpose, the outer rim of a disc 21 has a radially outwardly extending stop 22 being designed to serve as a contact area for the rim projection 20 such that the pressure applying surface 10 is spaced apart from an upper surface 23 of the outer rim of the disc 21. As FIG. 2 shows, the stop 22 can be formed by individual sub-stops which are arranged in a manner circumferentially distributed and spaced apart from one another and which then form the stop 22 in combination. The outer rim of the disc 21 is a ring-like bar which is integrally adapted to the inner component 17 along an axial central axis of the dispenser 1 and which can be varied with respect to height and/or width.

As is illustrated in particular in FIG. 4, the clamping area 16 can be formed by the diaphragm 14 such that, with diaphragm deformation under media pressure upon actuation (illustrated by dashed lines), no support of the diaphragm 14 against the outer rim of the disc 21 occurs. The entire surface area is therefore active as the pressure applying surface 10. A maximization of the size of the active pressure applying surface 10 is possible by using the clamping area 16 according to the invention for every surface area of a pressure applying surface 10.

Diaphragm deformation without contact with the outer rim of the disc 21 is also illustrated in FIG. 5. There, a distance x between the upper surface 23 of the outer rim of the disc 21 and a bottom side 24 of the diaphragm 14 is indicated by x>0. Also indicated is the effective diameter of the pressure applying surface 10 when the clamping area 16 according to the invention of the diaphragm 14 is used. Said distance x is indicated for the pressure limit in the valve ante chamber 9, which pressure limit leads to a partial displacement of the valve body 8 and is determined by the size of the pressure applying surface 10 and the design of the valve spring 13.

The outer rim of the disc 21 thus forms with the upper surface 23 a flat base for support, preferably partial boundary-side support, of the diaphragm 14 during diaphragm deformation under media pressure. For this purpose, the diaphragm 14 is elastically flexible for changing a chamber volume of the valve ante chamber 9.

FIG. 6 shows a second exemplary embodiment, in which the outer rim of the disc 21 is shaped as an annular projection which is designed to be higher than that in the first exemplary embodiment shown in FIG. 5. The height is selected such that the diaphragm 14 is supported on the upper surface 23 of the outer rim of the disc 21 or upon reaching the limit pressure in the valve ante chamber 9 by changing the chamber volume. The distance x is then 0, and, with the clamping area 16 according to the invention of the diaphragm 14 being used, the effective diameter of the pressure applying surface 10 is reduced by the size of the diameter width of the outer rim of the disc 21. As far as the diaphragm 14 is supported on the upper surface 23 of the outer rim of the disc 21, the force F exerted by the medium in the valve ante chamber 9 is introduced into the outer rim of the disc, and is not available as an effective pressure applying surface 10. A decrease in size of the pressure applying surface 10 brings that more force F has to be applied to achieve further diaphragm deformation, i.e. in order to be able to introduce more liquid into the valve ante chamber 9, this being necessary for reaching the pressure limit. This force/path behavior with the deflection of the diaphragm 14 can be used as tactile feedback during drop dispensing, in particular if, prior to reaching of the pressure limit, a decrease in size of the effective pressure applying surface 10 is determined via the height of the outer rim of the disc 21. By this, the reaching of the pressure limit and thus the dispensing of a drop through the opening of the discharge opening 6 can be indicated to the user via a haptic event, specifically that, when squeezing the reservoir container 2, the impending reaching of the pressure limit can be made tactile by increased pressure generation in the valve ante chamber 9 and thus as increase in movement resistance. According to the invention the drop dispensing can be set with tactile feel.

FIG. 7 and FIG. 8 show exemplary embodiments in which the force change point, which is detectable in a tactile manner, can be varied along the spring travel of the valve spring 13. The tactile feedback can be strengthened through selection of a particular wall thickness y1, y2 of the outer rim of the disc 21 (FIG. 8). By increasing wall thickness, the effective diameter of the pressure applying surface 10 is reduced and the increase in movement resistance is thus intensified, as FIG. 7 shows. FIG. 8 also shows the possibility of the wall thickness of the outer rim of the disc 21 being designed in an asymmetrical manner with respect to the axial central axis of the dispenser 1. This allows tilting of the valve body 8 with respect to the discharge opening 6, with the possibility of achieving a shearing-off of a drop being formed from the drop adapter 5.

The design of the valve seat 11 and the sealing edge 12 is illustrated in FIGS. 9a, 9b and FIGS. 10a, 10b for different sealings. A flat sealing is illustrated in FIGS. 9a, 9b. FIG. 9a shows a closed state of the outlet valve 7 with a flat sealing edge 12 for flat sealing. The open state is illustrated in FIG. 9b. FIG. 10a shows a closed state of the outlet valve 7 with a conical sealing edge 12 for conical sealing. The open state is illustrated in FIG. 10b. The arrangement of the valve seat 11 and the sealing edge 12 is preferably realized in the tip region of a preferably provided tubular extension of the dispensing adapter, designed here as a drop adapter 5, whereby the use for preservative-free formulations can be further improved.

FIG. 11 and FIG. 12 show the discharge head 3 with the respective to the venting path D, which is sealed off with respect to the reservoir container 2 and the inner space 25 thereof by means of a sealing device.

According to FIG. 11, a sealing disc 26 is provided for the sealing. The sealing disc 26 is curved in a concave manner with respect to the interior of the reservoir container 2. The sealing disc 26 abuts against a sealing edge 27 adjacent to a channel 28 for the venting path. The sealing edge 27 quasi forms a valve seat of a sealing disc 26 which functions in the manner of a check valve.

According to FIG. 12, a sealing plug 29 is provided as the sealing device. The sealing plug 29 has sealing lips 30, which likewise work in the manner of a check valve, for which purpose a valve seat may be formed on a wall 31.

The solution according to the invention is ultimately also able to be combined with solutions known from the prior art for configuring the dispenser 1 in liquid-conducting regions with bactericidal, that is to say bacteria-killing, or bacteriostatic, that is to say bacteria growth-preventing, surfaces, in order to eliminate or to avoid possibly occurring impurities.

Polyethylene (PE), a thermoplastic elastomer (TPE), polypropylene (PP) or a synthetic polymer, such as for example silicone, may be provided as material for the diaphragm.

It is furthermore possible in a known way for a protective cap to be put on the discharge head 3.

The dispenser 1 can be used for any type of fluid medium. It is possible for the medium to be able to be introduced with or without preservatives. Furthermore, it is particularly preferable for the height and/or radial width of the outer rim of the disc 21 and of the upper surface 23 thereof to be provided for the generation of moments for the tactile feedback of the diaphragm deformation when the chamber volume of the valve ante chamber 9 is changed in a manner dependent on a deflection movement of the diaphragm 14. It is furthermore preferable for an increase in movement resistance along a deformation path of the diaphragm 14 to be settable for drop dispensing. It is preferable for a force change point, which is detectable in a tactile manner, to be able to be varied along the spring travel of the valve spring 13. It is preferable for a stop-type pressure-displacement resistance, such as a pressure point, to be associated with the tactile feedback. It is preferable for the moments for the tactile feedback of the diaphragm deformation to be determined by the effective surface area of the pressure applying surface 10, which surface area is able to be varied in a manner dependent on the active pressure force.

There now also follows a function description of the dispenser 1 according to the invention:

The dispenser 1 is firstly filled by introducing medium into the reservoir container 2. Subsequently, the discharge head 3 with the drop system is preferably snapped on, as a lock 4, from above along the longitudinal axis. In order not to allow the forces that are in the process axially active to lead to an unwanted or permanently deforming bottle deformation, the bottle can be supported beneath a transfer ring 32 (cf. FIG. 3) during the snapping-on process. By way of the snapping-on process between the discharge head 3 and the reservoir container 2 toolless removal is not enabled.

The dispenser 1 is actuated by squeezing the reservoir container 2, whereby the latter can be elastically deformed and, as a result, the reservoir container volume is reduced. As a result of this, a positive inner pressure is built up. As a result of the inner pressure, medium or liquid is moved through the liquid path M. If the dispenser 1 is used in an upside-down position, for example as an eyedropper, said liquid path M then runs downstream. Here, the medium preferably passes through a narrow passage, the flow reducer 18, in the system. The narrowing of the cross section here induces an energy absorption as a result of backing-up and prevents that the media channel is flowed through too quickly, whereby a stream of medium when being discharged can be prevented in an effective manner. The flow reducer 18 can be matched in cross section to the media parameters (such as for example viscosity and surface tension). If the cross section for the medium is selected to be too narrow, the actuation force can increase up to the non-actuation force. In the rest position, the outlet valve 7 is closed off by way of the introduced spring force of the valve spring 13 and preferably a preloading of the diaphragm 14. The closing-off is preferably realized in a microbiologically sealed manner close to the discharge opening 6 (cf. FIGS. 9a, 9b and FIGS. 10a, 10b). The media pressure which is increasing during an actuation builds up a counter force F above the pressure applying surface 10 in the valve ante chamber 9 (cf. FIG. 4), whereby the diaphragm is deformed elastically in the direction of the reservoir container 2. At the same time, the increasing inner pressure in the interior 25 of the reservoir container 2 ensures that the elastically deformable sealing disc 26 is pressed in a self-intensifying manner against the sealing edge 27 of a preferably cylindrical extension beneath the microbiologically active filter arrangement 19 and, in this way, safely protects the vent path D from penetrating medium (cf. FIG. 11). As a result of the deformation of the diaphragm 14, the valve body 8 is moved axially in the same direction Y and the closing contact of the sealing surfaces 11, 12 is cleared upon reaching of a pressure limit, with which there is associated a particular displacement distance of the valve body 8 in the direction Y due to a diaphragm deformation. The resulting opening gap (cf. FIG. 9b, FIG. 10b) allows passage of medium. As soon as medium has accumulated to a sufficient amount at the discharge opening 6, this drips off under the action of gravitational force and, in this way, can be applied.

After the dripping-off, the user relieves the reservoir container 2 of load by releasing the actuation force. As a result of this, the pressure within the reservoir container 2 drops quickly. The valve spring 13 is then, possibly in combination with a preloading of the diaphragm 14, able to force the deformed diaphragm 14 back into its original position. Via the valve body 8, the sealing surfaces 11, 12 (cf. FIG. 9a, FIG. 10) then brought into a closed-off state again permanently until the next actuation. As a result of the media volume discharged, in combination with the restoration of the reservoir container 2, and the drop in the actuation force, the pressure conditions are reversed and, within the storage container 2, there then exists a negative pressure which additionally promotes and accelerates the closure of the sealing surface 11, 12. The negative pressure likewise ensures that the elastic sealing disc 26 can detach itself and, within an extremely short time, a subsequent flow of microbiologically filtered air by means of the filter 19 for compensation of the volume is permitted. Following the pressure and volume compensation, the sealing disc 26 (cf. FIG. 11), which is installed with preloading, prevents liquid from penetrating into the vent path.

For the function of the sealing disc 26, it is optionally also possible for use to be made of a sealing plug 29 (cf. FIG. 12), which achieves the venting function in a similar way by way of collapsing sealing lips 30. Here too, a media pressure-induced self-intensifying system is involved.

According to the invention, the dispenser 1 may be designed for actuation such that the increase in the media pressure above the pressure applying surface 10 in the valve ante chamber 9, whereby a counter force F builds up and the diaphragm 14 is deformed elastically in the direction of the reservoir container 2, is combined with a force change point, which is detectable in a tactile manner, along the spring travel of the valve spring 13. An increase in movement resistance during the compression of the reservoir container 2 for the purpose of drop dispensing provides haptically perceptible feedback, which forms, as a haptic event, the reaching of the pressure limit for opening the outlet valve 7. The force-displacement profile for the deflection of the diaphragm is able to be varied by a reduction in the effective diameter of the pressure applying surface 10 starting from a maximum effective diameter, due to the clamping area 16 according to the invention. Since the diaphragm 14 can be mounted on the outer rim of the disc 21 from the circumferential boundary, that is to say adjacent to the clamping area 16, while the valve body 8 displaces, at the center of the diaphragm 14, the upwardly projecting valve plunger 15 upwardly and downwardly, the displacement-force profile in the circumferential boundary region adjacent to the clamping area 16 is of lower extent than at the center of the diaphragm 14, with the possibility of the sensitive setting of a pressure point.

If diaphragm deformation is realized without contact with the outer rim of the disc 21, as illustrated in FIG. 5, then the outer rim of the disc 21 is designed geometrically such that, in the rest position and during the entire actuation (even at maximum diaphragm deformation due to the actuation inner pressure, that is to say attainment of the limit pressure), no contact takes place. During the entire actuation, the effective diaphragm diameter of the pressure applying surface is available. The entire surface area of the pressure applying surface 10 is preferably available, since the diaphragm 14 comes into abutment only laterally in the clamping region 16, that is to say substantially parallel to the force F (cf. FIG. 4, FIG. 5).

Diaphragm deformation with reduction in size of the pressure applying surface through abutment on the outer rim of the disc 21 is settable by way of plate boundary elevation. In terms of dimensions, the outer rim of the disc height is able to be formed such that, in the rest position, there is no contact between the outer rim of the disc 21 and the diaphragm inner side 24. Upon actuation, firstly the entire diaphragm diameter of the pressure application surface 10 is available for the valve opening. If appropriate, at just a minimal deformation of the diaphragm 14, this can come down onto the outer rim of the disc 21 and, in this way, the effective diaphragm diameter can be slightly reduced, whereby the active force is then too small to achieve further deformation of the diaphragm 14 due to partial introduction of the force F into the outer rim of the disc 21 (FIG. 6).

In addition or as an alternative to the outer rim of the disc elevation, the wall thickness of the outer rim of the disc 21 can be increased. The outer rim of the disc inner diameter is thus reduced (cf. FIG. 7). This design makes it possible for the effective diaphragm diameter to be reduced by up to 70% in comparison with the starting diameter. This can improve the controllability of the drop dispensing even further and can thereby prevent overflowing (stream formation).

An asymmetrical formation of the outer rim of the disc 21 (FIG. 8) allows tilting of the valve plunger 15 about an angle (Z° in FIG. 8) and, in this way, one-sided opening of the outlet valve 7, that is to say a passage for the medium can be released only partially. The outer rim of the disc asymmetry can be up to 8-fold in extent.

The invention claimed is:

1. A dispenser for a liquid, having a reservoir container for receiving medium, having a discharge head which is able to be mounted to the reservoir container and has a discharge opening for discharging medium from the reservoir container, having a discharge valve which is associated with the discharge opening and which has a preloaded valve body which delimits a valve ante chamber by way of a pressure applying surface formed on a diaphragm, wherein the pressure applying surface has at the outside a positionally fixed clamping area, and having a pressure compensation channel which opens into the reservoir container and has a microbiologically active filter arrangement inserted in said channel, wherein the pressure compensation channel is separated from a media path from the reservoir container via the valve ante chamber to the discharge opening, characterized in that the pressure applying surface has, as a clamping area, a cap-like rim projection which is able to be mounted at the inside on an outer rim of a disc of an inner component of the discharge head, and the outer rim of the disc has a radially outwardly extending stop which forms a support surface for the rim projection such that the pressure applying surface is spaced apart from an upper surface of the outer rim of the disc, wherein the valve body forms the diaphragm such that a valve plunger, bearing at the upper side a sealing element for closing off the discharge opening, rises therefrom, and wherein, for the design of the positionally fixed clamping area, the diaphragm is, at a boundary side, fastened in a fluid-tight manner by way of laser welding to an inner component of the discharge head.

2. Dispenser as claimed in claim 1, wherein, by means of a valve spring, force is applied to the valve body in the direction of the discharge opening.

3. Dispenser as claimed in claim 1, wherein the stop comprises individual sub-stops which are arranged spaced apart from one another.

4. Dispenser as claimed in claim 1, wherein the outer rim of the disc provides with a head surface a flat base for support of the diaphragm during diaphragm deformation under media pressure.

5. Dispenser as claimed in claim 1, wherein the outer rim of the disc is a ring-like bar which is integrally formed on the inner component about an axial central axis of the discharge device and which is able to be varied with respect to height and/or width.

6. Dispenser as claimed in claim 5, wherein the height of the bar of the outer rim of the disc is selected such that, prior to or upon reaching a pressure limit in the valve chamber, the diaphragm is supported on the upper surface as a result of the chamber volume being changed.

7. Dispenser as claimed in claim 1, wherein an effective diameter of the pressure applying surface is settable via the height and/or radial width of the outer rim of the disc and of the upper surface thereof.

8. Dispenser as claimed in claim 1, wherein the height and/or radial width of the outer rim of the disc and of the upper surface thereof are provided for the generation of moments for the tactile feedback of the diaphragm deformation when the chamber volume of the valve ante chamber is changed in a manner dependent on a deflection movement of the diaphragm.

9. Dispenser as claimed in claim 8, wherein a wall thickness of the outer rim of the disc is provided in an asymmetrical manner with respect to the axial central axis of the dispenser.

10. Dispenser as claimed in claim 8, wherein an increase in movement resistance along a deformation path of the diaphragm is settable for drop dispensing.

11. Dispenser as claimed in claim 8, wherein a force change point, which is detectable in a tactile manner, is able to be varied along the spring travel of a valve spring.

12. Dispenser as claimed in claim 8, wherein an stop-type pressure-displacement resistance, such as a pressure point, is associated with the tactile feedback.

13. Dispenser as claimed in claim 8, wherein the moments for the tactile feedback of the diaphragm deformation are determined by the effective surface area of the pressure applying surface, which surface area is able to be varied in a manner dependent on the active pressure force.

14. Dispenser as claimed in claim 1, wherein the pressure equalization channel is sealed off with respect to the reservoir container and the inner space thereof by a sealing device.

15. Dispenser as claimed in claim 14, wherein the sealing device is designed as a sealing disk or sealing plug.

16. Dispenser as claimed in claim 1, wherein provision is made of a flow reducer via which medium is able to be forced into the medium path from the reservoir container.

17. Dispenser as claimed in claim 1, wherein the discharge head comprises as an outer component a dispensing adapter which has a tubular extension and which is a drop adapter for the dispensing eye drops.

\* \* \* \* \*